US012779080B2

(12) United States Patent
Rossettini et al.

(10) Patent No.: US 12,779,080 B2
(45) Date of Patent: Nov. 3, 2026

(54) PURIFYING DEVICE

(71) Applicant: D-ORBIT S.P.A., Fino Mornasco (IT)

(72) Inventors: Luca Rossettini, Fino Mornasco (IT); Marco Cazzaniga, Fino Mornasco (IT); Massimiliano Zandonini Gutris, Fino Mornasco (IT)

(73) Assignee: D-ORBIT S.P.A., Fino Mornasco (IT)

( * ) Notice: Subject to any disclaimer, the term of this patent is extended or adjusted under 35 U.S.C. 154(b) by 374 days.

(21) Appl. No.: 18/560,259

(22) PCT Filed: May 12, 2022

(86) PCT No.: PCT/IB2022/054434
§ 371 (c)(1),
(2) Date: Nov. 10, 2023

(87) PCT Pub. No.: WO2022/238957
PCT Pub. Date: Nov. 17, 2022

(65) Prior Publication Data
US 2024/0277885 A1 Aug. 22, 2024

(30) Foreign Application Priority Data
May 13, 2021 (IT) ........................ 102021000012404

(51) Int. Cl.
*A61L 9/20* (2006.01)
*C02F 1/32* (2023.01)
*F24F 8/22* (2021.01)

(52) U.S. Cl.
CPC ................ *A61L 9/20* (2013.01); *C02F 1/325* (2013.01); *A61L 2202/11* (2013.01);
(Continued)

(58) Field of Classification Search
CPC ........ A61L 9/20; A61L 2202/11; C02F 1/325; C02F 2201/328; C02F 2301/028; C02F 2303/04; F24F 8/22
See application file for complete search history.

(56) References Cited

U.S. PATENT DOCUMENTS

2009/0081340 A1 3/2009 Forney
2015/0114912 A1 4/2015 Taghipour
(Continued)

FOREIGN PATENT DOCUMENTS

JP 2018140001 A 9/2018

OTHER PUBLICATIONS

International Search Report and Written Opinion issued in corresponding International Application No. PCT/IB2022/054434 dated Aug. 17, 2022.

*Primary Examiner* — Georgia Y Epps
*Assistant Examiner* — Hanway Chang
(74) *Attorney, Agent, or Firm* — Husch Blackwell LLP

(57) ABSTRACT

A fluid purifying device includes inlet and emission openings, an outer tube having a first end on a first side of the device relative to a reference plane, the inlet opening at the first end of the outer tube, an inner tube, within the outer tube and having a second end on a second side of the device, opposite to the first side relative to the reference plane, the emission opening at the second end of the inner tube, an intermediate tube between the outer and inner tubes defining a fluid path between the inlet and emission openings, the fluid path including a first stretch between the outer and intermediate tubes, a second stretch between the intermediate and inner tubes, and a third stretch within the inner tube, and a UV-C radiation source within the outer tube to irradiate the fluid at least along the first stretch.

19 Claims, 4 Drawing Sheets

(52) U.S. Cl.
CPC .. *C02F 2201/328* (2013.01); *C02F 2301/028* (2013.01); *C02F 2303/04* (2013.01); *F24F 8/22* (2021.01)

(56) References Cited

U.S. PATENT DOCUMENTS

| | | | | |
|---|---|---|---|---|
| 2019/0225509 | A1* | 7/2019 | Dhiman .................. | C02F 1/325 |
| 2020/0230270 | A1 | 7/2020 | Taghipour | |

* cited by examiner

PURIFYING DEVICE

CROSS REFERENCES

This application is a U.S. National Phase Application of International Application No. PCT/IB2022/054434, filed May 12, 2022, which claims priority to Italian Application No. 102021000012404, filed May 13, 2021, the disclosures of each of which are expressly incorporated by reference herein in their entireties.

TECHNICAL FIELD

The present disclosure relates to a purifying device and, more particularly, to a device for eliminating or neutralizing pathogens in a fluid.

BACKGROUND

Purification techniques are known in the field, using ultraviolet germicidal irradiation (UVGI), which uses ultraviolet radiation (UV) with wavelengths comprised within the UV-C band (between 100 and 280 nanometers) that modifies the DNA or RNA of microorganisms and therefore prevents them from reproducing or being harmful.

The use of this purification technology involves for example the irradiation, by means of germicidal lamps that emit UV-C radiation, in a confined environment such as a closed room, an air conditioning system or a water tank. An example of a UV-C radiation source commonly used for this purpose in the prior art is represented by mercury vapor lamps, that emit germicidal radiation at different wavelengths in the UV-C band.

The degree of microbial inactivation achievable by ultraviolet radiation depends on several factors, including in particular the dosage of UV-C radiation applied to the fluid to be purified. The dosage is given by the product between the intensity of UV-C radiation, measured in [$W/m^2$], and the exposure time to UV-C radiation.

The radiation intensity factor can be appropriately adjusted by providing UV-C radiation sources having a sufficient radiant power relative to the environment to be irradiated.

The radiation exposure time factor is particularly relevant in dynamic purification systems wherein the fluid is set in motion with respect to the UV-C radiation source. In these cases, in fact, the need to maximize the irradiation time of the fluid to be purified, which involves in turn the need to lengthen as much as possible the fluid path exposed to UV-C radiation, collides with the dimensional restrictions of the system, sometimes set to contain the overall dimensions and/or the manufacturing costs.

The Applicant has perceived the need in the field to create fluid purifying devices that are highly effective in inactivating pathogens, but also meet the requirements of compactness, portability and cost-effectiveness typically associated with devices suitable for domestic and/or professional use.

Another need identified by the Applicant in relation with UV-C radiation emission devices for fluid purification purposes, is that of safety. As known, in fact, prolonged exposure to UV-C rays can be harmful to the skin and eyes, as well as causing the degradation of some materials susceptible to oxidation when exposed to UV-C.

In this regard, the Applicant has perceived the need to confine UV-C radiation so that it only hits the fluid to be purified and does not reach people or objects that may be present in the proximity of the purifier, when in use.

In light of the above, the Applicant has therefore addressed the technical problem of creating a fluid purifying device that has a high microbial inactivation effectiveness, and that is at the same time characterized by minimized dimensions, manufacturing costs as low as possible and high safety.

SUMMARY

The present disclosure therefore concerns, in a first aspect thereof, a fluid purifying device including a fluid inlet opening and a fluid emission opening, the device further including an outer tube having a first end positioned on a first side of the device relative to a reference plane, the fluid inlet opening being defined at the first end of the outer tube, an inner tube, arranged within the outer tube and having a second end positioned on a second side of the device, opposite to the first side relative to the reference plane, the fluid emission opening being defined at the second end of the inner tube, an intermediate tube, arranged between the outer tube and the inner tube so as to define a mandatory and continuous fluid path between the inlet opening and the emission opening, the path comprising a first stretch confined between the outer tube and the intermediate tube, a second stretch confined between the intermediate tube and the inner tube and a third stretch confined within the inner tube, and a UV-C radiation source arranged within the outer tube so as to irradiate the fluid at least along the first stretch of the fluid path.

In the following description and in subsequent claims, the "reference plane" is identified as an ideal plane that cuts in two, preferably substantially in half, the outer tube and/or the device perpendicular to a longitudinal axis of the device.

In the following description and in subsequent claims, "longitudinal axis of the device" is meant to indicate an axis arranged in the length direction of the device and coinciding with a central axis of the outer tube and/or of the intermediate tube and/or of the inner tube of the device.

In the following description and in subsequent claims, "longitudinal" is meant to indicate a direction parallel to or coincident with the longitudinal axis of the device.

The Applicant notes that the "matryoshka" configuration of the tube assembly of the purifying device advantageously allows the total length of the fluid path to be maximized for the same total length of the device.

The longer length of the fluid path is reflected in an increase, with the same flow rate imposed by the feeding member, of the residence time of the fluid within the device and, therefore, of its exposure to germicidal radiation emitted by the UV-C radiation source. The longer exposure time to UV-C radiation allows the level of inactivation of the microbial component present in the fluid passing through the device to be increased.

Thanks to the configuration devised by the Applicant, the device of the disclosure is compact, particularly suitable for example for use in domestic or public environments for air purification, or can be connected to domestic or industrial water networks for water purification.

Advantageously, moreover, since the UV-C radiation source is positioned in the outer tube, it primarily hits the fluid passing in the first stretch of fluid path and possibly, as better specified thereafter, the fluid passing in the second stretch of fluid path. The inner tube, on the other hand, confines ultraviolet radiation within the device, preventing it from spreading outside through the emission opening.

Overall, the above-outlined purposes of high microbial inactivation effectiveness, minimized footprint, low implementation costs and high safety are thus achieved.

The present disclosure may have one or more of the preferred features listed below, which can be combined with one other depending on the application requirements.

Preferably, the path includes a first passage for the fluid between the first stretch and the second stretch.

Preferably, the path includes a second passage for the fluid between the second stretch and the third stretch.

Preferably, the outer tube is in fluid communication with the intermediate tube through the first passage.

Preferably, the intermediate tube is in fluid communication with the inner tube through the second passage.

Preferably, a first end of the outer tube, positioned on the first side of the device relative to the reference plane, is closed except at the inlet opening.

Preferably, a second end of the outer tube, positioned on the second side of the device relative to the reference plane, is closed except at the emission opening.

Preferably, a first end of the intermediate tube, positioned on the first side of the device relative to the reference plane, is closed.

Preferably, the outer tube and the intermediate tube have respective second ends, positioned on the second side of the device relative to the reference plane, at which the first passage for the fluid is defined.

Preferably, a second end of the intermediate tube, positioned on the second side of the device relative to the reference plane, is open at least at the first passage and at the emission opening.

Preferably, the inner tube has a first end, positioned on the first side of the device relative to the reference plane, at which the second passage for the fluid is defined.

Preferably, the first end of the inner tube is closed except at the second passage.

Preferably, a second end of the inner tube, positioned on the second side of the device relative to the reference plane, is fully or partially open so as to define the emission opening.

The fluid path preferably has a serpentine shape, when observed in a longitudinal section of the purifying device.

Preferably, the first stretch of the fluid path extends between the inlet opening and the first passage.

Preferably, the second stretch of the fluid path extends between the first passage and the second passage.

Preferably, the third stretch of the fluid path extends between the second passage and the emission opening.

Preferably, a length of the intermediate tube is less than a length of the outer tube.

Preferably, a length of the inner tube is less than a length of the intermediate tube.

Preferably, the second end of the outer tube and the second end of the inner tube are substantially at the same distance from the reference plane.

Preferably, the second end of the intermediate tube is at a shorter distance from the reference plane than the second end of the outer tube and/or than the second end of the inner tube.

The first passage for the fluid is in such case preferably defined, thanks to this difference in longitudinal extension between the outer tube and the intermediate tube, above the second end of the intermediate tube. Preferably, the first passage for the fluid is defined between the second end of the intermediate tube and the second end of the outer tube.

Preferably, an outer diameter of the intermediate tube is less than an inner diameter of the outer tube.

Preferably, an outer diameter of the inner tube is less than an inner diameter of the intermediate tube.

It follows that an inner diameter of the inner tube is less than an inner diameter of the intermediate tube, which in turn is less than an inner diameter of the outer tube.

Preferably, the outer tube has a lumen with a substantially circular cross-section.

Preferably, the intermediate tube has a lumen with a substantially circular cross-section.

Preferably, the inner tube has a lumen with a substantially circular cross-section.

Preferably, the substantially circular cross-section of at least one between the outer tube, the intermediate tube and the inner tube, has a constant radius at least for most of the longitudinal extension of the outer tube, of the intermediate tube and of the inner tube, respectively.

In embodiments, at least one between the intermediate tube and the inner tube preferably includes a portion, more preferably located at the respective first end, in which the substantially circular cross-section of the respective lumen has a variable radius.

Preferably, the outer tube and intermediate tube are substantially coaxial.

Preferably, the first stretch of the fluid path extends along a first duct, defined between the outer tube and the intermediate tube.

Preferably, the first duct extends between the inlet opening of the device and the first passage for the fluid.

Preferably, the first duct has a cross-section having a substantially annular shape at least for most of the longitudinal extension of the outer tube.

More preferably, the cross-section of the first duct is substantially annular in shape at least for the entire longitudinal extension of the intermediate tube.

Preferably, the cross-section of the first duct is substantially circular in shape where the intermediate tube is absent.

Preferably, the cross-section of the first duct is substantially circular in shape near the first end of the outer tube, for example, in a region comprised between the inlet opening and the first end of the intermediate tube.

Preferably, the intermediate tube and inner tube are substantially coaxial.

Preferably, the second stretch of the fluid path extends along a second duct, defined between the intermediate tube and the inner tube.

Preferably, the second duct extends between the first passage and the second fluid passage.

Preferably, the second duct has a cross-section having a substantially annular shape at least for most of the longitudinal extension of the intermediate tube.

More preferably, the cross-section of the second duct is substantially annular in shape at least for the entire longitudinal extension of the inner tube.

Preferably, the cross-section of the second duct is substantially circular in shape where the inner tube is absent.

For example, the cross-section of the second duct is substantially circular in shape in a region between the first end of the intermediate tube and the first end of the inner tube.

Preferably, the third stretch of the fluid path extends along a third duct, defined by the inner tube.

Preferably, the third duct extends between the second passage and the emission opening of the device.

Preferably, the third duct has a cross-section having a substantially circular shape.

Preferably, the outer tube, the intermediate tube and the inner tube are substantially coaxial.

Advantageously, the entire fluid path extends along ducts having an annular or circular shape, which minimizes the occurrence of turbulence in the flow.

Preferably, at any position along the longitudinal axis of the device, the cross-section of the first duct has a larger area than the cross-section of the second duct.

Preferably, at any position along the longitudinal axis of the device between the first and second ends of the inner tube, the cross-section of the second duct has a larger area than the cross-section of the third duct.

The provision of gradually narrower cross-sections for the flowing of fluid allows the flow rate of the fluid to be increased as it advances along the fluid path, due to the Venturi effect.

Therefore, preferably the fluid passes in the first stretch of the fluid path at a first flow rate, then in the second stretch of the fluid path at a second flow rate higher than the first flow rate, and lastly in the third stretch of the fluid path at a third flow rate higher than the second flow rate.

This advantageously allows to have longer residence times of the fluid in the first stretch of the fluid path (and secondarily in the second stretch of the fluid path) where the UV-C radiation source is located so as to optimize the germicidal action by the source. On the other hand, the residence times in the third stretch (where the fluid is not exposed to germicidal radiation emitted by the UV-C radiation source) are minimized so as to speed up the outflow of the purified fluid through the emission opening.

Preferably, a ratio between an inner radius of the inner tube and an inner radius of the outer tube is less than or equal to ½, more preferably between ⅕ and ½ endpoints included, even more preferably between ¼ and ½ endpoints included, even more preferably of about ⅓.

In the present description and in subsequent claims, all numerical values indicating quantities, parameters, percentages and so forth shall be construed to be preceded in all circumstances by the term "about" unless otherwise indicated. Further, all ranges of numerical values are meant to be endpoints included unless otherwise indicated, and include all possible combinations of maximum and minimum numerical values and all possible intermediate ranges, other than those specifically set forth below.

The Applicant has found that that the provision of an inner tube and an outer tube having such proportions is advantageous both in terms of fluid dynamics and in terms of confinement of the UV-C radiations within the device, to the benefit of the safety thereof.

Preferably, a ratio between a longitudinal extension of a non-tapered portion of the intermediate tube and an inner radius of the intermediate tube is equal to or greater than 4, more preferably equal to or greater than 5, more preferably comprised between 5 and 25 endpoints included, more preferably between 5 and 20 endpoints included, more preferably between 5 and 10 endpoints included.

In the present description and the attached claims, "non-tapered portion of the intermediate tube" is meant to indicate the portion of the intermediate tube having a substantially circular cross-section of constant radius.

The Applicant has analytically verified that the provision of an intermediate tube having such proportions, especially in combination with an inner tube and an outer tube having the proportions detailed above, allows to significantly attenuate the fraction of reflected UV-C radiation that manages to reach the third duct and the emission opening of the device.

Preferably, at its first end, the intermediate tube has a tapered portion having a cross-section with decreasing radius moving towards the inlet opening of the device.

The tapered portion is in such case preferably defined between a connection region, having a cross-section with maximum radius and closer to the reference plane, and a vertex, corresponding to the first end of the intermediate tube and farthest from the reference plane.

In such case, preferably, at the tapered portion of the intermediate tube, a cross-section of the first duct gradually decreases by moving from the first end of the intermediate tube to the connecting region of the tapered portion.

The presence of the tapered portion in the termination of the intermediate tube improves the fluid dynamics at the beginning of the first stretch of the fluid path near the inlet opening, allowing a gradual increase in the fluid rate due to the Venturi effect, and minimizing the occurrence of turbulence in the flow lines.

Preferably, the tapered portion comprises a conical wall forming with the longitudinal axis of the device an angle comprised between 20° and 50°, more preferably between 30° and 45°.

In addition to the advantages in terms of improved fluid dynamics, the provision of a tapered portion having the conical shape further promotes, especially in combination with an intermediate tube having the above-described proportions, the attenuation of the reflected fraction of UV-C radiation capable of reaching the third duct.

From an analytical and mathematical assessment carried out by the Applicant it has in particular been found that in embodiments including an inner tube, an intermediate tube and an outer tube having the above-detailed geometrical proportions, wherein the intermediate tube has at an end thereof a conical tapered portion configured as indicated above, only a reflected fraction comprised between 0.1 and 1% of the radiation emitted by the source of UV-C radiation manages to reach the emission opening of the device, with clear advantages in terms of safety for people or objects that may be close to the device.

Preferably, the UV-C radiation source is arranged so as to irradiate the fluid parallel to the direction of flow along the fluid path (i.e. along a longitudinal direction of the device). In particular, the UV-C radiation source is arranged so as to irradiate the fluid parallel to the direction of flow along the first stretch of the fluid path (and, possibly, along the second stretch of the fluid path). This advantageously allows the microbial inactivation power to be optimized.

The Applicant believes indeed that the microbial inactivation power is maximum when the UV-C radiation source is oriented parallel to the fluid flow, and minimum (although present) when the UV-C radiation source is oriented perpendicular to the fluid flow.

In the present description and the attached claims, directional expressions such as "parallel" and the like, when used in connection with irradiation by means of a UV-C radiation source, indicate that the UV-C radiation source is oriented such that an axis of the light cone emitted by the source is arranged parallel to a given direction.

In the present description and the attached claims, "light cone" is meant to indicate, consistently with the common meaning of such expression in the field, a cone-shaped light beam emitted by the UV-C radiation source.

Preferably, the radiation emitted by the UV-C radiation source has a wavelength greater than or equal to 255 nm.

Above such wavelength value the risk that UV-C radiation generates ozone, which is as known a dangerous gas for human health, is minimized.

More preferably, the radiation emitted by the UV-C source has a wavelength greater than or equal to 270 nm.

Above such wavelength value, the risk of ozone generation is even more decreased.

Even more preferably, the radiation emitted by the UV-C radiation source has a wavelength greater than or equal to 275 nm.

Above such wavelength value, the risk of ozone generation is substantially annulled.

Preferably, in order to optimize the germicidal effectiveness of UV-C radiation, the radiation emitted by the UV-C radiation source has a wavelength less than or equal to 300 nm.

More preferably, the radiation emitted by the UV-C radiation source has a wavelength less than or equal to 290 nm.

Even more preferably, the radiation emitted by the UV-C radiation source has a wavelength less than or equal to 285 nm.

Below such wavelength value, the germicidal effectiveness of UV-C radiation is maximized.

Preferably, the UV-C radiation source is configured to emit at least 90% of the radiant power at a wavelength comprised between 270 nm and 290 nm.

More preferably, the UV-C radiation source is configured to emit at least 90% of the radiant power at a wavelength comprised between 275 nm and 285 nm.

Within this narrow band of wavelengths, the emitted radiation is optimized both in terms of germicidal effectiveness and in terms of safety in connection with ozone generation.

Preferably, the UV-C radiation source is arranged so as to directly irradiate the first duct and/or the second duct.

Preferably, the UV-C radiation source is arranged so as to directly irradiate the fluid along the first stretch and/or along the second stretch of the fluid path.

Preferably, the UV-C radiation source is arranged so as to irradiate at most indirectly the fluid along the third stretch of the fluid path.

Preferably, the UV-C radiation source is arranged so as to irradiate at most indirectly the third duct.

In the present description and the attached claims, "directly irradiate", "directly hit" or similar expressions used in connection with UV-C irradiation are meant to indicate that at least a fraction of the luminous radiation emitted by the UV-C source directly hits a given component of the device, without undergoing light reflections or bounces on a reflective surface. The same expressions "directly irradiate", "directly hit" and the like are therefore also applicable to direct irradiation with the interposition of one or more transparent elements, which do not cause substantial reflection phenomena.

In the present description and the attached claims, "indirectly irradiate", "indirectly hit" or similar expressions are used in connection with components of the device that are invested only by a fraction of luminous radiation that has undergone at least one light reflection or bounce on a reflective surface, or at most are not invested by any luminous radiation emitted by the source.

Preferably, the UV-C radiation source comprises a first UV-C emitter arranged at the first end of the outer tube.

Preferably, the first emitter is arranged so as to directly irradiate the first duct.

Preferably, the first UV-C emitter is positioned within the first duct.

Preferably, the first UV-C emitter is positioned outside of the second duct.

Preferably, the first UV-C emitter is positioned radially outside of the second duct.

In the present description and the attached claims, "radial direction" is meant to indicate a direction orthogonal to the longitudinal axis of the device.

Preferably, the first UV-C emitter is positioned outside of the third duct.

Preferably, the first UV-C emitter is positioned radially outside of the third duct.

Preferably, the first UV-C emitter is arranged so as to irradiate at most indirectly the fluid along the third stretch of the fluid path.

Preferably, the first UV-C emitter is arranged so as to irradiate at most indirectly the third duct.

Preferably, the first UV-C emitter is positioned near an inner surface of the outer tube of the device.

Preferably, the first UV-C emitter is oriented so as to irradiate the first duct parallel to the longitudinal axis of the device.

In this way, the UV-C radiation source is advantageously arranged so as to directly irradiate the fluid passing along the first stretch of the fluid path within the first duct, in particular near the inlet opening. Since, as explained above, in the first stretch of the fluid path there is a lower flow speed, this arrangement of the source is particularly advantageous as it allows the fluid to be irradiated for a comparatively longer time than if it were arranged to irradiate the second or third stretch of the fluid path, even if they were all made of the same length, thereby achieving a greater germicidal effectiveness.

Such arrangement also allows the best germicidal effectiveness to be obtained especially in liquid, for example water, purification devices, in which the flow rates involved are comparatively much lower than those that are reached when a gaseous fluid is moved, thereby achieving a high level of purification even with a single UV-C emitter.

Alternatively or in addition, the UV-C radiation source includes a second UV-C emitter arranged at the second end of the outer tube.

The duplication of emitters increases the dose of irradiated UV-C radiation and increases germicidal effectiveness.

Preferably, the second UV-C emitter is positioned so as to straddle the first fluid passage.

In other words, the second UV-C emitter is preferably positioned so as to go across the first fluid passage.

More preferably, in such case the second UV-C emitter is arranged so as to directly irradiate the first and second stretches of the fluid path, thereby prolonging the exposure of the fluid to UV-C radiation.

Preferably, the second UV-C emitter is arranged so as to directly irradiate the first duct and the second duct.

Preferably, the second UV-C emitter is positioned outside of the third conduit.

Preferably, the second UV-C emitter is positioned outside of the inner tube.

Preferably, the second UV-C emitter is positioned radially outside of the inner tube.

Preferably, the second UV-C emitter is arranged so as to irradiate at most indirectly the fluid along the third stretch of the fluid path.

Preferably, the second UV-C emitter is arranged so as to irradiate at most indirectly the third duct.

Preferably, the second emitter is positioned near an outer surface of the inner tube of the device.

Preferably, the second emitter is oriented so as to irradiate the first duct and/or the second duct parallel to the longitudinal axis of the device.

In a particularly preferred embodiment, the UV-C radiation source comprises both the first emitter and the second emitter.

The combined use of two emitters simultaneously achieves doubling of the total emission intensity and a prolongation of the exposure of the fluid to radiation, thereby maximizing the total dose of UV-C radiation absorbed by the fluid and, as a consequence, germicidal effectiveness. This configuration is especially suitable for the purification of gaseous fluids, which are generally flowed into the device at higher speeds than liquid fluids and which, all other conditions being equal, are thus irradiated for less time.

With the positioning described above for the first and second emitter (when present), the UV-C emitted radiation directly hits the fluid passing in the first stretch and possibly in the second stretch of the fluid path, whereas it hits at most indirectly the fluid passing in the third stretch of the fluid path. In this way, the third tube advantageously acts as a shielding element of direct UV-C radiation, confining it inside the device and reducing the fraction of reflected UV-C radiation capable of exiting through the emission opening. In this way, the risk that the UV-C radiation hits people or objects that may be present near the emission opening of the device is significantly reduced.

Preferably, indeed, within the inner tube there is no UV-C emitter.

Preferably, the device is devoid of emitters arranged so as to directly irradiate the fluid along the third path within the third duct.

Preferably, the device is devoid of emitters arranged so as to directly irradiate the third duct.

Preferably, as discussed above, the UV-C radiation intensity measured at the emission opening of the device is less than 1%, more preferably less than 0.1%, with respect to the UV-C radiation intensity measured near the first emitter and/or the second emitter.

Preferably, the UV-C radiation source is configured to generate a total radiant UV flux between 50 and 500 mW.

More preferably, the UV-C radiation source is configured to generate a total radiant UV flux between 80 and 350 mW.

Even more preferably, the UV-C radiation source is configured to generate a total radiant UV flux between 100 and 200 mW.

Preferably, the UV-C radiation source includes one or more UV-C LEDs.

LED-type UV-C emitters are associated with numerous advantages over known technologies, such as the aforementioned mercury vapor lamps. Among these advantages, the following are for example mentioned:

- LEDs have very small dimensions and are therefore more versatile and easily adaptable to different application solutions;
- LEDs easily lend themselves to be integrated into compact, lightweight technologies, possibly also battery powered, and operating in "on demand" mode;
- compared to less advanced technologies, LEDs are also easily drivable, modular and controllable even remotely using a suitably configured electronics;
- the emission of the LED is concentrated in one direction and with a light cone which angle ranges from 90° to 150°, and this allows to collimate the emission beam by means of relatively simple optics, in order to direct the beam on a precise target and minimizing losses;
- LEDs allow significant energy savings compared to other irradiation technologies;
- the emission of LEDs is not polluting, since they do not contain mercury vapors or other harmful components;
- LEDs have a much longer life than emitters of other types; an LED has an average shelf-life of about 10-15000 hours, the average shelf-life of a mercury vapor lamp being about a third; and finally,
- LEDs are instantaneously capable to provide maximum power without any heating time; therefore, unlike mercury vapor lamps, LEDs are activated immediately and can perform an almost unlimited number of on and off sequences without any deterioration of their emission features.

In embodiments, the device is configured to purify a gaseous fluid. For example, in such case the fluid can be ambient air.

In other embodiments, the device is configured to purify a liquid fluid. For example, in such case the fluid may be water.

In embodiments (and preferably when the fluid to be purified is gaseous), the device further includes a feeding member configured to feed the fluid within the inlet opening.

When the fluid to be purified is gaseous, the fluid feeding member in the device preferably includes a fan.

In case the fluid to be purified is a liquid, the fluid feeding member in the device preferably includes a pump.

Preferably, when the fluid to be purified is liquid, the device is configured to be connected to a liquid supply hydraulic circuit. In particular, in such case the device is preferably connected to the hydraulic circuit at the inlet opening and at the emission opening.

In embodiments, when the fluid to be purified is liquid, it is preferably fed into the device by exploiting the pressure of the hydraulic circuit for the liquid supply. In such case, the device may therefore be devoid of the fluid feeding member in the device.

Preferably, the device further includes a filter positioned near the inlet opening, more preferably upstream of the inlet opening with reference to a direction of movement of the fluid along the fluid path.

Preferably, the device comprises a lid.

Preferably the lid is in the form of a circular crown.

The lid is preferably configured to close a second end of the device, positioned on the second side relative to the reference plane, except at the emission opening.

Preferably, the first passage for the fluid is defined as an annular opening defined between an edge of the second end of the intermediate tube and the lid.

Preferably, the second passage for the fluid includes a plurality of holes made at the first closed end of the inner tube, for example in a closing cap applied to the first end of the inner tube.

Preferably, the outer tube, the intermediate tube and/or the inner tube are made of a material that is not transparent to UV-C radiation.

Preferably, the outer tube, the intermediate tube and/or the inner tube are made of a material reflective of UV-C radiation.

Preferably, the inner surface of the outer tube, the inner and outer surfaces of the intermediate tube, and the inner and outer surfaces of the inner tube are reflective to UV-C radiation.

Preferably, the outer tube, the intermediate tube and/or the inner tube are made of a material having a reflectance to UV-C radiation comprised between 70% and 100% endpoints included, more preferably between 70% and 90% endpoints included, even more preferably between 80% and 90% endpoints included.

Preferably, the outer tube, the intermediate tube and the inner tube are made of a material selected from aluminum, PTFE and special UVC reflective metal alloys, being preferably aluminum, preferably having a reflectance to UV-C radiation comprised between 70% and 100% endpoints included, more preferably between 70% and 90% endpoints included, even more preferably between 80% and 90% endpoints included.

The Applicant has verified in analytical manner that such reflectance values achieve an advantageous balance between the need to propagate UV-C radiation for a long time in order to maintain a high germicidal power of the device and the need to maximize the number of light reflections and bounces in order to sufficiently attenuate the intensity of the fraction of radiation that manages to reach the emission opening of the device.

Preferably, one or more between the outer tube, the intermediate tube and the inner tube comprise, internally and/or externally, a reflective coating including a photocatalytic activator. Photocatalytic activators can activate the decomposition of microbes and pollutants, breaking them down into harmless substances.

For example, such an adjuvant can be in the form of a paint or a resin containing a $TiO_2$-based photocatalytic activator.

The use of such coating allows the overall performance of the purifying device to be increased.

Preferably, the device further comprises an external tubular shell, designed to protect the assembly of tubes and possibly to improve the aesthetics of the device.

Preferably, the device is shaped as a vertical turret. This conformation is advantageous especially for use as an air purifier, and is particularly suitable for domestic use as it allows a considerable saving of lateral space.

When the device is shaped like a vertical turret, a support is preferably provided on the first side of the device, at a base end of the same.

When the shell is present, this includes at least one opening at a first end thereof, which is positioned at the bottom of the device. Such opening allows the fluid to access the inlet opening of the outer tube, which would otherwise be closed because of the device resting on the ground.

When present, the filter is positioned at the opening in the shell.

Preferably, the intermediate tube is fixed to the outer tube by means of fasteners suitably located along the longitudinal extension of the intermediate tube. Such fasteners are preferably configured, in terms of shape and size, to hinder as little as possible the passage of fluid within the first duct and include, for example, one or more brackets, hooks, screws.

Preferably the inner tube is constrained to the lid of the device at its second end, the first end of the inner tube being instead floating. This assembly ensures that there are no elements of hindrance to the fluid within the second duct.

In preferred embodiments, the device further comprises at least one electronic module.

Such electronic module preferably comprises one or more electronic components selected from a processing unit, a user interface and a communication module (preferably wireless) configured, for example, for the internet connection.

These aspects are merely illustrative aspects of the innumerable aspects associated with the present disclosure and should not be deemed as limiting in any manner. These and other aspects, features and advantages of the present disclosure will become apparent from the following detailed description when taken in conjunction with the referenced figures.

BRIEF DESCRIPTION OF THE DRAWINGS

Further features and advantages of the present disclosure will be best understood from the following detailed description of preferred embodiments thereof, made in an indicative and not limiting manner with reference to the attached drawings, which are to be considered schematic and not to scale representations. In such drawings.

DETAILED DESCRIPTION

Figure 2:
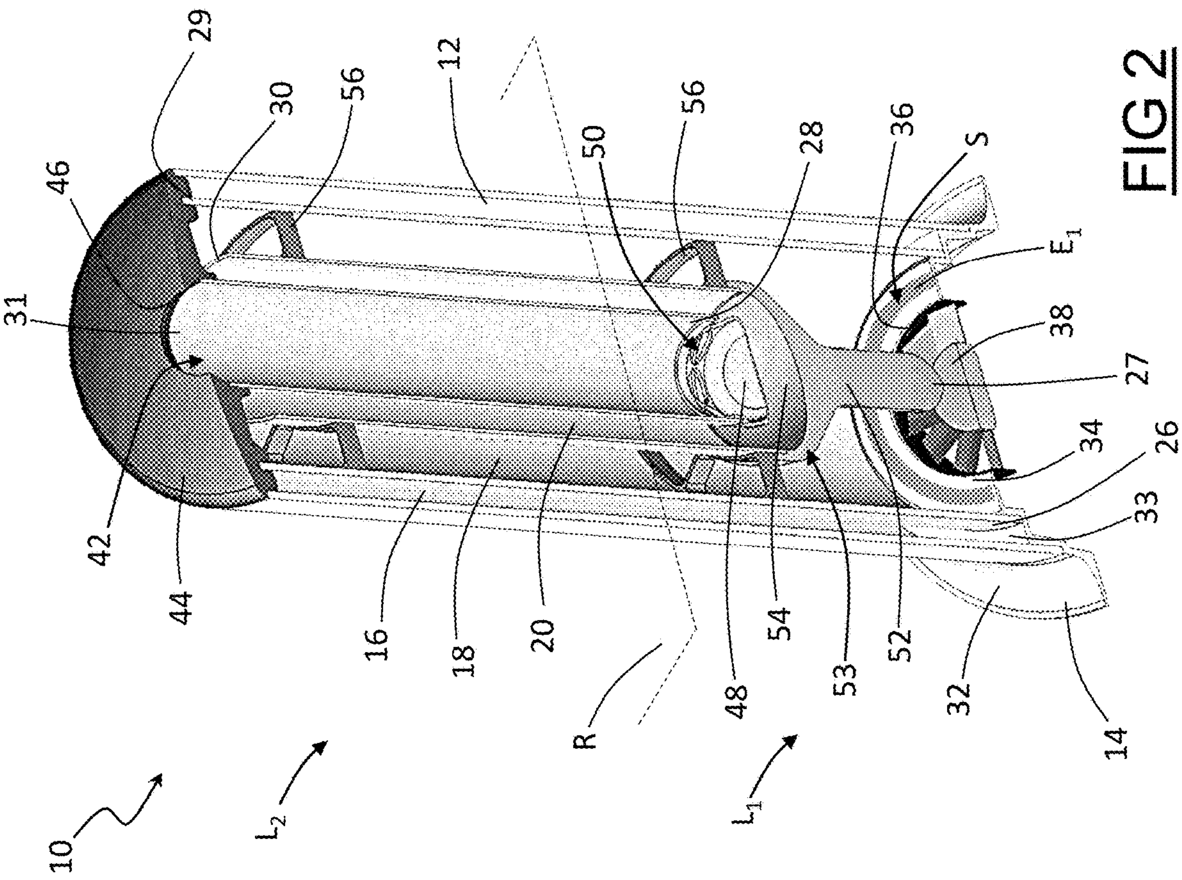
FIG. 2 is a perspective view in longitudinal section of the device of FIG. 1.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

In the following detailed description numerous specific details are set forth in order to provide a thorough understanding of the present disclosure. However, it will be understood by those skilled in the art that the present disclosure may be practiced without these specific details. For example, the present disclosure is not limited in scope to the particular type of industry application depicted in the figures. In other instances, well-known methods, procedures, and components have not been described in detail so as not to obscure the present disclosure.

The headings and sub-headings used herein are intended only for general organization of topics within the present disclosure and are not intended to limit the disclosure of the technology or any aspect thereof. In particular, subject matter disclosed in the “Background” may include novel technology and may not constitute a recitation of prior art. Subject matter disclosed in the “Summary” is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the “Detailed Description” section of this specification are hereby incorporated by reference in their entirety.

With reference to the attached FIGS. 1-7, a purifying device is hereby described according to preferred embodiments of the disclosure, such device being indicated in the various figures with numerical reference 10.

The purifying device 10, sometimes in short device 10, is by way of example made as a turret configured for vertical positioning, standing on a floor or on a horizontal support.

In the various figures an ideal reference plane R, cutting the device 10 substantially at half its height perpendicularly to a longitudinal axis A (traced in FIGS. 1 and 3) of the same device, is schematically indicated by means of a dotted line. Such reference plane R allows to distinguish a first side $L_1$ of the device, which in this case is the one below the plane R and closer to the ground, and a second side $L_2$ of the device, which is located above the plane R.

Figure 1:
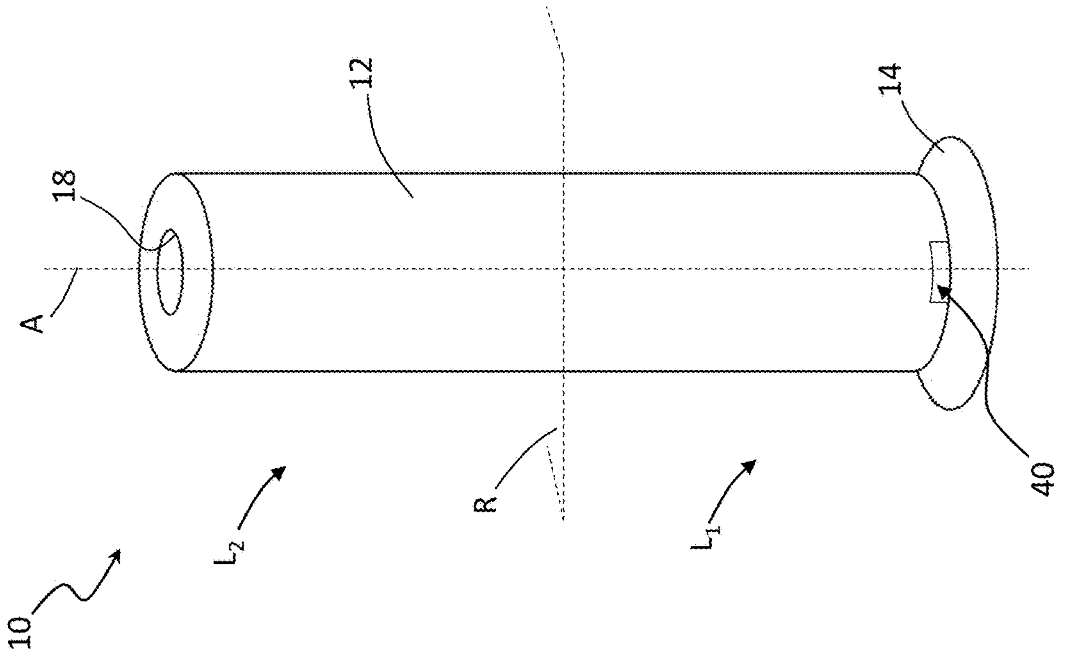
FIG. 1 is a perspective view of a device according to a first preferred embodiment of the disclosure.

Externally, as seen in particular in FIG. 1, the device 10 is equipped with a shell 12 of substantially cylindrical shape, which protects the components enclosed therein and can be used to provide the device with the desired aesthetic appearance in terms of possible materials, finishes and colors that can be used.

To improve its vertical stability, the device can be equipped with a support 14 on its first side $L_1$, to which the shell 12 is bound at its lower edge.

Figure 4:
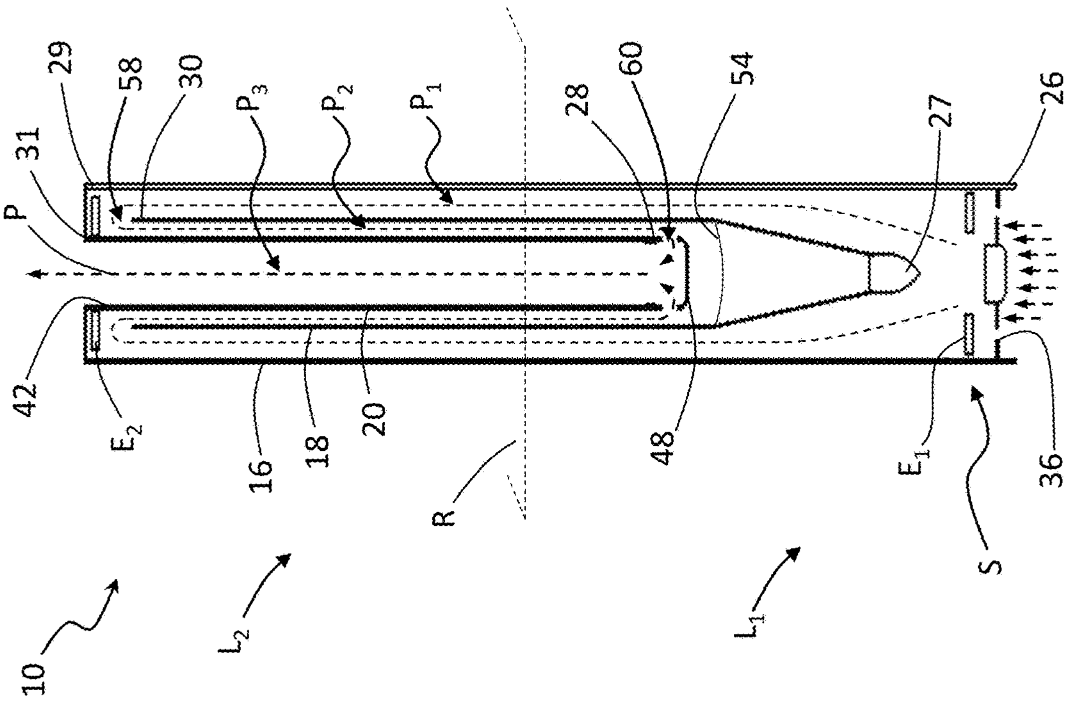
FIGS. 3 and 4 are schematic views in longitudinal section of the device of FIG. 1, illustrated with some components removed for the sake of clarity.
Figure 3:
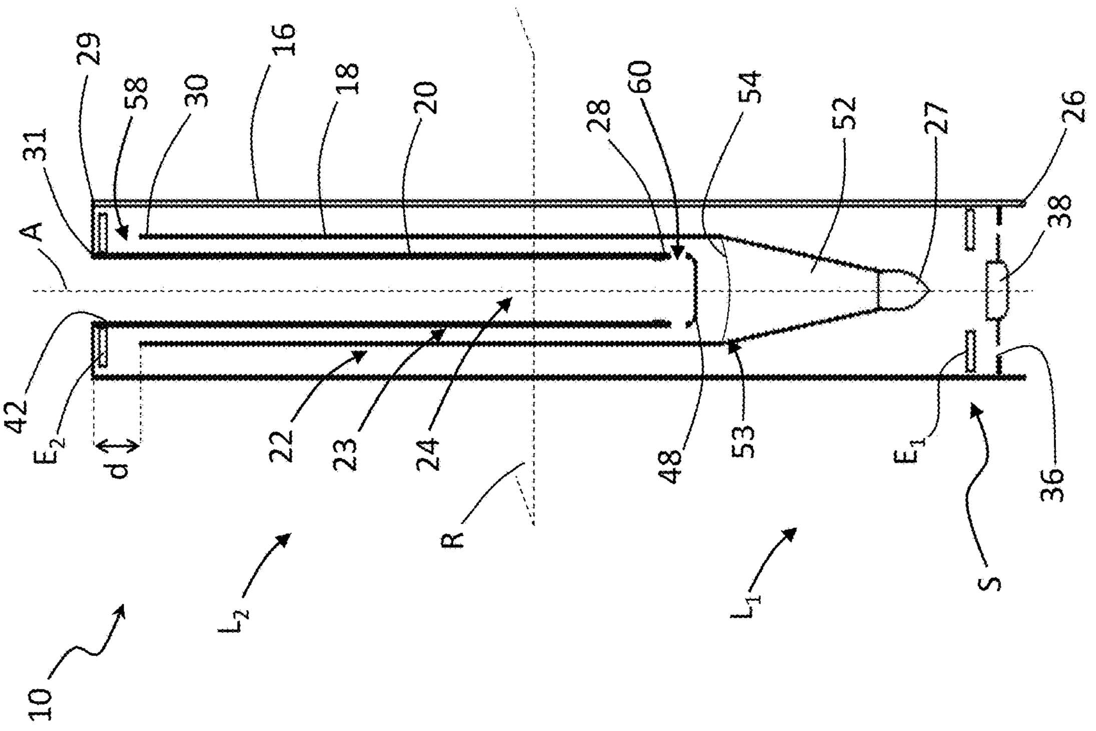
Figure 5:
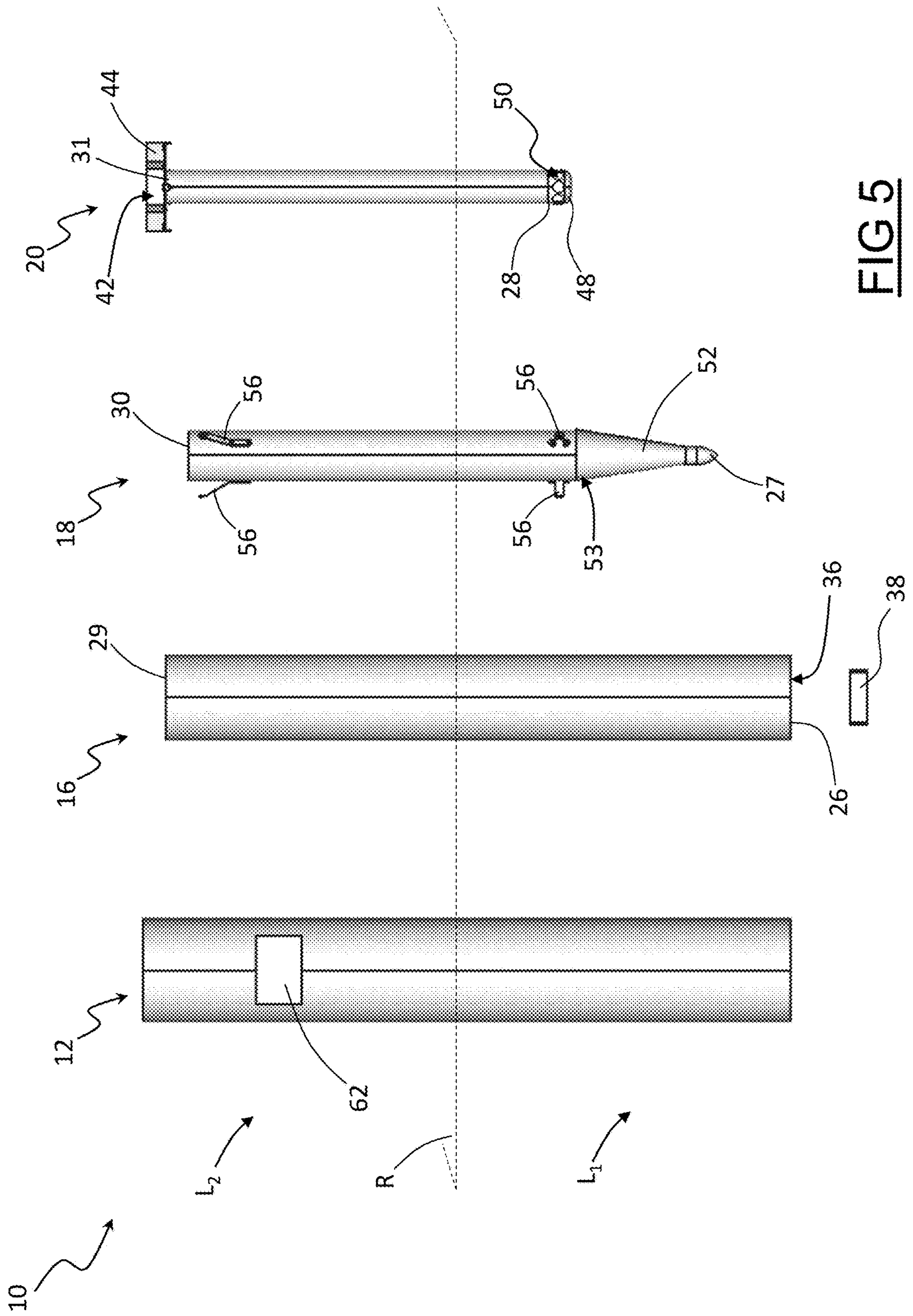
FIG. 5 is an exploded view of components of the device according to the disclosure.
Figure 7:
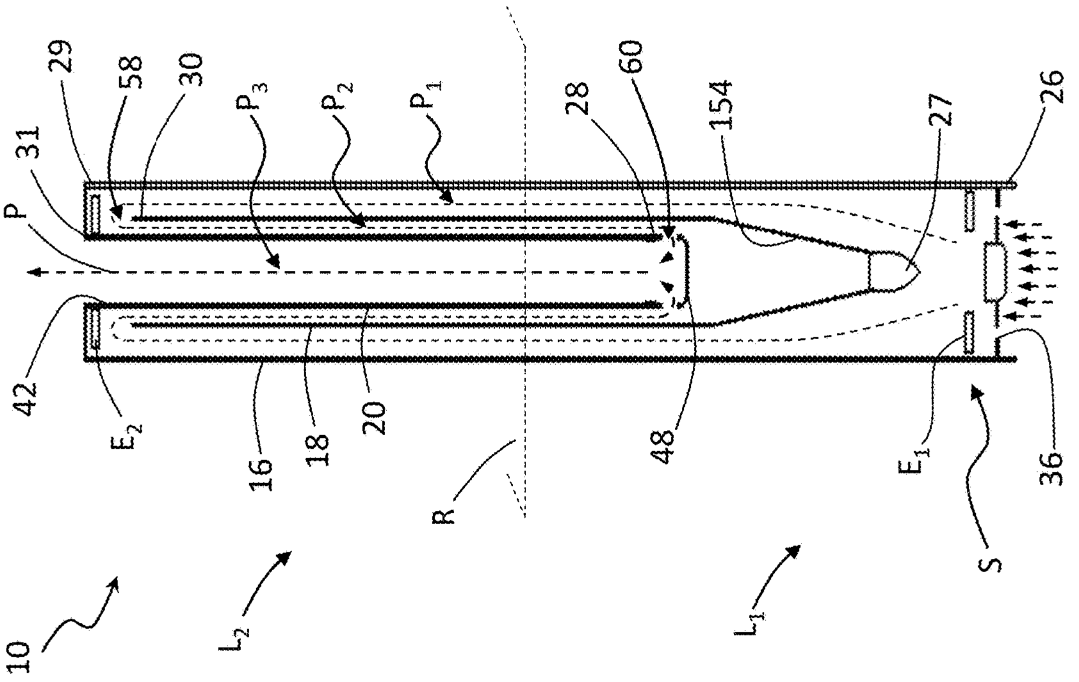
FIGS. 6 and 7 are schematic views in longitudinal section of a device according to a second preferred embodiment of the present disclosure, illustrated with some components removed for the sake of clarity.
Figure 6:
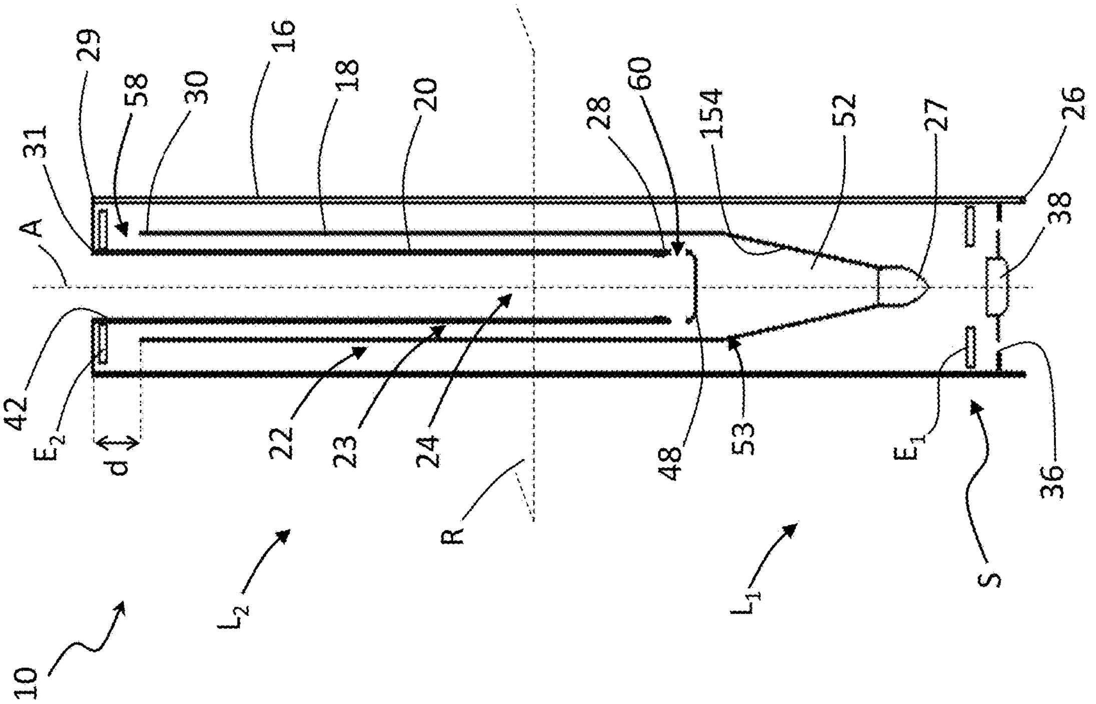

In FIGS. 2-4, the device 10 is shown sectioned along a longitudinal plane in order to show its internal configuration. FIGS. 3-4 schematically illustrate only some internal components of a first embodiment of device 10; FIGS. 6-7 are views, similar to those of FIGS. 3-4, which schematically illustrate some internal components of a second embodiment of device 10. In FIGS. 3-7 in particular shell 12 and base 14 have been removed for ease of illustration. The main components of the device 10 according to both the described embodiments are also shown in exploded view in FIG. 5.

Inside, device 10 includes an outer tube 16, an intermediate tube 18 and an inner tube 20 mutually arranged as a "matryoshka", i.e. inside one another.

In particular, the intermediate tube 18 is arranged within the outer tube 16, and the inner tube 20 is arranged within the intermediate tube 18. The three tubes 16, 18, 20 have an internal lumen with a substantially circular cross-section of constant radius—except for a tapered portion of the intermediate tube 18, described in detail hereinafter—and are arranged coaxially along axis A, traced in FIGS. 3 and 6.

The outer tube 16, the intermediate tube 18 and the inner tube 20 extend between respective first ends 26, 27, 28, positioned on the first side $L_1$ of device 10, and respective second ends 29, 30, 31, positioned on the second side $L_2$ of device 10 opposite the first side $L_1$.

The first end 26 of the outer tube 16 is directly fixed to support 14, which as visible in FIG. 2 is made in the form of an annular element comprising a radially outer support base 32 with annular profiles 33, 34 gradually closer to the reference plane R moving radially inside the support 14.

At the first end 26 of the outer tube 16, the device has an inlet opening 36 for the fluid to be purified. Such inlet opening 36 is in particular delimited by the radially innermost annular profile 34 of the support 14, so that the first end 26 of the outer tube 16 is closed except for the inlet opening 36.

A fluid feeding member 38 is operationally arranged at the inlet opening 36 so as to force the inlet of fluid to be purified within the outer tube 16 of device 10 through the inlet opening 36.

In the preferred embodiment illustrated in the various figures, device 10 is configured to purify a gaseous fluid such as ambient air. The feeding member 38 is preferably embodied by a fan, suitably sized according to the range of flow rates that are desirably achieved within the device 10.

To allow access of the fluid to be purified to the inlet opening 36, which would otherwise be closed between support 14 and the ground on which it rests, an opening 40 is provided through the shell 12 and part of the base 14. Such opening 40 is illustrated in FIG. 1 as a window with straight edges and limited circumferential extension, but can be alternatively made of other shapes and/or sizes according to the specifications of the fan and the dimensions of the tubes 16, 18, 20. For example, an opening could be envisaged circumferentially extended substantially along the entire shell 12.

Especially in air purification devices, such as the one shown, it is advantageous to provide a filter (not shown) at the opening 40, in order to purify the air from dust or other macroscopic impurities prior to the purification operation to be carried out within the device 10 as will be described below. Device 10 also includes, on its second side $L_2$ relative to the reference plane R, an emission opening 42, through which the fluid is released once it has been purified. The emission opening 42 is made at the second end 31 of the inner tube 20, thus being on top of the device 10.

There is also provided an annular lid 44 covering the second end 29 of the outer tube 16 and touching the second end 20 of the inner tube 20 (see FIG. 2), such second ends 29 and 31 being substantially at a same longitudinal distance from the reference plane R. Lid 44 is provided with a central 46 hole that leaves the 42 emission opening of device 10 open. The shape of the lid 44 can be modified compared to what is shown in FIGS. 1 and 2 also according to aesthetic requirements.

The inner tube 20 is fixed to lid 44 at its second end 31. The first end 28 of the inner tube 20, on the other hand, is free and closed by a cap 48 provided with a plurality of holes 50.

As mentioned above, at its first end 27 the intermediate tube 18 includes a tapered portion 52, defined between a connecting region 53, having a cross-section of maximum radius and equal to that of the remaining part of the intermediate tube 18, and a vertex corresponding to the first end 27 of the intermediate tube 18 and indicated by the same reference. The tapered portion 52 has therefore a cross-section of gradually decreasing radius moving from the connecting region 53 to the first end 27 of the intermediate tube 18. Such tapered portion 52 can have a curved outer profile, as shown in FIG. 2, or a substantially conical or frustoconical profile, as in the more schematic representation of FIGS. 3-4 and 6-7 and in the exploded view of FIG. 5.

More specifically, the first end 27 of intermediate tube 18 is closed by the tapered portion 52, which substantially constitutes a cap. The tapered portion 52 can be made integral with the remaining part of the intermediate tube 18, or it can be fixed thereto, as in the case illustrated in the various figures.

In the embodiment of FIGS. 3-4, the tapered portion 52 preferably has a solid cross-section, thereby defining a bottom wall 54 of intermediate tube 18 having a planar or slightly concave shape. In the embodiment shown in FIGS. 6-7, the tapered portion 52 comprises an elongated internal cavity that follows the external profile of the same, the bottom wall 154 of the intermediate tube 18 having in such case a much more pronounced concavity.

The second end 30 of the intermediate tube 18 is open and is located at a distance from the reference plane R lower than the second ends 29, 31 of the outer tube 16 and of the inner tube 20. In other words, the second end 30 of the intermediate tube 18 is at a distance “d” from the lid 44 (shown in FIGS. 3 and 6).

The intermediate tube 18 is maintained in place by a plurality of coupling elements 56, protruding from its outer wall and configured to attach to be fixed to the inner wall of the outer tube 16. Coupling elements 56 can be made of various shapes, including, for example, semicircular frames (FIG. 2), or bracket elements (FIG. 5).

The dimensions of each of the three tubes 16, 18, 20 are suitably selected, as defined in the introductory part of this application, so as to allow the aforementioned “matryoshka” arrangement, ensuring in particular the presence (FIGS. 3 and 6) of a first duct 22, defined between the external tube 16 and the intermediate tube 18 and of a second duct 23, defined between the intermediate tube 18 and the inner tube 20, within which the fluid can flow in a continuous and confined manner. There is also provided a third duct 24 corresponding to the inner lumen of the inner tube 20.

The first duct 22 and the second duct 23 are in fluid communication with each other through a first passage 58 made at the second ends 29, 30 of the outer tube 16 and of the intermediate tube 18. In particular, the first passage 58 is defined in the space of width “d” defined between the second end 30 of the intermediate tube 18 and the lid 44.

The second duct 23 and the third duct 24 are in fluid communication with each other through a second passage 60 made at the first end 27 of the inner tube 20. The second passage 60 consists in particular of holes 50 in the cap 48 provided on the first end 27 of the inner tube 20.

Between the inlet opening 36 and the first end 27 of the intermediate tube 18, the first duct 22 has a cross-section of circular shape. Between the first end 27 of the intermediate tube 18 and the first passage 58, the first duct 22 has a cross-section of annular shape.

Between the first passage 58 and the first end 28 of the inner tube 20, the second duct 23 has a cross-section of annular shape, whereas between the first end 28 of the inner tube 20 and the bottom wall 54, 154 the second duct 23 has a cross-section of circular shape.

The third duct 24 is instead entirely circular in cross-section.

The thus configured ducts 22, 23, 24 define a continuous and mandatory fluid path P for the fluid between the inlet opening 36 and the emission opening 42. FIG. 4 shows in a completely schematic manner the course of the fluid path P in a longitudinal section of the device.

The fluid path P comprises a first stretch $P_1$, defined within the first duct 22 between the inlet opening 36 and the first passage 58, a second stretch $P_2$, defined within the second duct 23 between the first passage 58 and the second passage 60, a third stretch $P_3$, defined within the third duct 24 between the second passage 60 and the emission opening 42. Fluid path P then goes through the first passage 58, which connects the first stretch $P_1$ to the second stretch $P_2$, and the second passage 60, which connects the second stretch $P_2$ to the third stretch $P_3$.

As illustrated, in a longitudinal section of device 10, the fluid path P takes on a substantially serpentine shape.

From the diagram of FIGS. 4 and 7 it can be appreciated how the configuration of tubes of the device, arranged and interconnected as described above, allows to obtain a very long fluid path P of fluid in relation to the overall dimensions of the device 10.

In an exemplary embodiment, the device 10 has a height comprised between 100 and 130 cm, with an outer diameter (corresponding to the outer diameter of the shell) comprised between 15 and 25 cm. The device 10 is therefore very compact and particularly suitable for home use.

While advancing along fluid path P, the cross-section of the ducts gradually decreases, and this causes the rate of the fluid that is passing to increase due to the Venturi effect, as explained in the introductory part of the present document.

Therefore, the first stretch $P_1$ of the fluid path P is the one in which the fluid has the absolute lower rate, whereas the third stretch $P_3$ of the fluid path P, closer to the emission opening 42, is the one in which the fluid has the absolute higher rate.

The fluid is purified as it passes along fluid path P by UV-C irradiation, operated by a source S of UV-C radiation positioned within the outer tube 16. The source S of UV-C radiation is preferably configured to emit at least 90% of the radiant power at a wavelength comprised between 270 nm and 290 nm, more preferably between 275 nm and 285 nm, and is therefore capable of exerting a particularly effective germicidal action, for the reasons set out in the introductory part of the application.

In the illustrated preferred embodiment, the UV-C radiation source S includes a first emitter $E_1$ arranged at the first end of outer tube 16 so as to directly irradiate the first duct 22.

More in particular, the first emitter $E_1$ is oriented so as to irradiate the fluid parallel to the direction it takes up along the first stretch $P_1$ of fluid path P, or in other words parallel to the wall of the outer tube 16 and to the longitudinal axis A of the device. For example, the first emitter $E_1$ is fixed on the annular profile 34 of support 14 near an inner surface of the outer tube 16 of the device 10 (FIG. 2).

The positioning of the first emitter $E_1$ to directly irradiate the first duct 22, in which the fluid flows at the lowest rate, allows to obtain the maximum germicidal effectiveness as the time of exposure of the fluid to radiation is maximized.

The source S of UV-C radiation also includes a second emitter $E_2$, arranged at the second end of the outer tube 16.

In this case, the second emitter $E_2$ is advantageously arranged to directly irradiate, parallel to the flow direction of the fluid and to the longitudinal axis A of the device, both the first duct 22, and the second duct 23. This effect of simultaneous irradiation of the two ducts 22, 23 is achieved by placing the second emitter $E_2$ above and straddling the intermediate tube 18, straddling the first fluid passage 58. For example, the second emitter $E_2$ is attached on the inside of lid 44, near an outer surface of the inner tube 20 of the device 10.

In the presence of the second emitter $E_2$, the fluid is also directly irradiated when it passes through the second duct 23, although at a higher speed than when passing in the first duct 22; moreover, the direct irradiation by the second emitter $E_2$ is added to that of the first emitter $E_1$ to which the fluid passing in the first duct 22 is exposed. Overall, therefore, the use of two emitters $E_1$ and $E_2$ positioned in this way significantly increases the germicidal effectiveness of the device 10.

The positioning of the illustrated emitters $E_1$ and $E_2$ is also advantageous in terms of safety of the device 10. In fact, in the absence of additional emitters arranged so as to directly irradiate the inner tube 20 and thus the third duct 24, the UV-C radiation emitted by the first and second emitters $E_1$ and $E_2$ directly hits the fluid passing in the first and second stretches $P_1$ and $P_2$ of the fluid path, whereas it hits at most indirectly the one passing in the third stretch $P_3$. The wall of the third tube 20 effectively shields the direct radiation emitted by the second emitter $E_2$, thereby significantly reducing the fraction of reflected UV-C capable of exiting the device 10 through the emission opening 42 and causing damages to people or objects.

In order to maximize the attenuation of reflected UV-C radiation capable of reaching the emission opening of the device 10, the second conduit 23 advantageously has the proportions described in the introductory portion of this application, in combination with the provision of a tapered portion 52 having an angled conical wall as more fully described above.

The Applicant has verified in analytical manner the safety of the device 10 by means of computer simulations.

Using the program Ray-Optics Simulator, two-dimensional geometric models of device 10 have been built, representative of it longitudinal cross-section, varying each time some significant geometric parameters thereof.

In the two-dimensional models of device 10, the presence of a point source of UV-C radiation has been simulated, positioned at the second end of the outer tube within the first duct, and having a luminous emission at 360° in the simulation plane. Device walls having 100% reflectivity were considered in the simulations.

From such simulations, the Applicant has found that complying to the preferred geometric proportions of the device, detailed in the introductory part of the present application, only a fraction smaller than 0.1% of the radiation emitted by the emitters manages to indirectly reach the emission opening 42 of the device 10, more in particular always as a result of no less than 10-20 reflections on inner surfaces of the device 10.

The first and second emitters $E_1$ and $E_2$ advantageously include one or more UV-C LED modules. For example, a single UV-C LED strip can be provided, arranged circumferentially along the annular profile 34 of support 14 (first emitter $E_1$, FIG. 2), or on the inside of lid 44 (second emitter $E_2$). Alternatively, several discrete modules can be provided, regularly distributed along the inner perimeter of the outer tube 16.

Device 10 also includes electronics configured in particular for powering the device 10, for controlling and modulating the LED emitters $E_1$, $E_2$, and for driving the fluid feeding member 38.

The electronics preferably include a processing unit (not visible), for example arranged in a dedicated housing formed in lid 44 of the device, and a user interface 62 shown in FIG. 5. The user interface 62 is for example programmed to allow the user to activate or deactivate the device 10, to manage how it is used, to set alarms or timers, to extract statistics and feedback, to modify or update the interface software, and the like. Preferably, the electronics also includes a wireless communication module (not visible) configured to interface with an internet network, so as to allow the device to be controlled and data to be extracted even remotely.

Although a purifying device optimized for a gaseous fluid has been described in detail, the detailed description given above also applies, mutatis mutandis, to a purifying device for a liquid fluid, introducing changes within reach of the skilled person in the art.

Specifically, when used as a water purifier, the device is installed where possible between the water inlet piping and the outlet tap, in which case it is necessary to seal all the interfaces between the device and the piping.

For water purification, the device is small enough to allow home installations, and the capability of processing water at the flow rate out of the tap (typically about 200 liters/hour). In addition, unlike known water purifiers based on the use of filters, the device according to the disclosure advantageously allows the water to be purified without depleting the mineral component, thus maintaining unaltered its properties.

The preferred embodiments of the disclosure have been described above to explain the principles of the present disclosure and its practical application to thereby enable others skilled in the art to utilize the present disclosure. However, as various modifications could be made in the constructions and methods herein described and illustrated without departing from the scope of the present disclosure, it is intended that all matter contained in the foregoing description or shown in the accompanying drawings, including all materials expressly incorporated by reference herein, shall be interpreted as illustrative rather than limiting. Thus, the breadth and scope of the present disclosure should not be limited by the above-described exemplary embodiment but should be defined only in accordance with the following claims appended hereto and their equivalents.

The invention claimed is:

1. A fluid purifying device comprising:

an inlet opening for a fluid and an emission opening for the fluid;

an outer tube having a first end positioned on a first side of the fluid purifying device relative to a reference plane, the inlet opening for the fluid being defined at the first end of the outer tube, an inner tube, arranged within the outer tube and having a second end positioned on a second side of the device, opposite to the first side relative to the reference plane, the emission opening for the fluid being defined at the second end of the inner tube;

an intermediate tube, arranged between the outer tube and the inner tube so as to define a mandatory and continuous fluid path between the inlet opening and the emission opening, the fluid path including a first stretch confined between the outer tube and the intermediate tube, a second stretch confined between the intermediate tube and the inner tube and a third stretch confined within the inner tube;

a source of UV-C radiation arranged within the outer tube so as to irradiate the fluid at least along the first stretch of the fluid path; and wherein the source of UV-C radiation is arranged so as to directly irradiate the fluid along at least one of the first stretch and the second stretch of the fluid path, and so as to irradiate at most indirectly the fluid along the third stretch of the fluid path, and wherein the device is devoid of any UV-C emitter disposed within the inner tube.

2. The fluid purifying device of claim 1, wherein the fluid path includes a first passage for the fluid between the first stretch and the second stretch and a second passage for the fluid between the second stretch and the third stretch, the outer tube being in fluid communication with the intermediate tube through the first passage, and the intermediate tube being in fluid communication with the inner tube through the second passage.

3. The fluid purifying device of claim 2, wherein the first passage is defined at respective second ends, positioned on the second side of the fluid purifying device relative to the reference plane, of the outer tube, and of the intermediate tube.

4. The fluid purifying device of claim 2, wherein the second passage is defined at the first end of the outer tube, positioned on the first side of the fluid purifying device relative to the reference plane, of the inner tube.

5. The fluid purifying device of claim 1, wherein the first stretch of the fluid path extends within a first duct defined between the outer tube and the intermediate tube, the second stretch of the fluid path extends within a second duct defined between the intermediate tube and the inner tube, and the third stretch of the fluid path extends within a third duct defined by the inner tube, wherein, at any position along a longitudinal axis of the fluid purifying device, a cross-section of the first duct has a larger area with respect to a cross-section of the second duct, and wherein, at any position along the longitudinal axis of the fluid purifying device comprised between the first and second ends of the inner tube, the cross-section of the second duct has a larger area with respect to a cross-section of the third duct.

6. The fluid purifying device of claim 5, wherein a ratio between an inner radius of the inner tube and an inner radius of the outer tube is less than or equal to ½.

7. The fluid purifying device of claim 6, wherein the ratio between the inner radius of the inner tube and the inner radius of the outer tube is between ⅕ and ½, endpoints included.

8. The fluid purifying device of claim 5, wherein a ratio between a longitudinal extension of a non-tapered portion of the intermediate tube and an inner radius of the intermediate tube is equal to or greater than 4.

9. The fluid purifying device of claim 8, wherein the ratio between the longitudinal extension of the non-tapered portion of the intermediate tube and the inner radius of the intermediate tube is between 5 and 25, endpoints included.

10. The fluid purifying device of claim 1, wherein at a first end thereof, positioned on the first side of the fluid purifying device relative to the reference plane, the intermediate tube has a closed tapered portion having a cross-section with a decreasing radius moving towards the inlet opening of the fluid purifying device.

11. The fluid purifying device of claim 10, wherein the tapered portion comprises a conical wall forming with a longitudinal axis of the fluid purifying device an angle between 20° and 50°.

12. The fluid purifying device of claim 11, wherein the conical wall forms with the longitudinal axis of the fluid purifying device an angle between 30° and 45°.

13. The fluid purifying device of claim 1, wherein the source of UV-C radiation is arranged so as to irradiate the fluid parallel to a flow direction along the fluid path.

14. The fluid purifying device of claim 1, wherein a radiation emitted by the source of UV-C radiation has a wavelength greater than or equal to 255 nm and less than or equal to 300 nm.

15. The fluid purifying device of claim 14, wherein the radiation emitted by the source of UV-C radiation has a wavelength greater than or equal to 270 nm and less than or equal to 290 nm.

16. The fluid purifying device of claim 1, wherein the source of UV-C radiation comprises at least one of:

a first UV-C emitter, arranged at the first end of the outer tube; and a second UV-C emitter, arranged at the second end of the outer tube.

17. The fluid purifying device of claim 16, wherein the second UV-C emitter is arranged at the second end of the outer tube so as to irradiate the first stretch and the second stretch of the fluid path.

18. The fluid purifying device of claim 1, further comprising a feeding member configured to feed the fluid to be purified within the inlet opening.

19. The fluid purifying device of claim 1, wherein at least one of the outer tube, the intermediate tube, and the inner tube are made of a material that is not transparent to UV-C radiation and has a reflectivity to UV-C radiation between 70% and 100%, endpoints included.

* * * * *